United States Patent
Lee et al.

(10) Patent No.: US 11,242,444 B2
(45) Date of Patent: Feb. 8, 2022

(54) TRIAZINE COMPOUNDS, COMPOSITIONS, AND METHODS

(71) Applicants: Duk Hi Lee, Anaheim, CA (US); Arthur Lee, San Carlos, CA (US)

(72) Inventors: Duk Hi Lee, Anaheim, CA (US); Arthur Lee, San Carlos, CA (US)

(*) Notice: Subject to any disclaimer, the term of this patent is extended or adjusted under 35 U.S.C. 154(b) by 242 days.

(21) Appl. No.: 16/679,544

(22) Filed: Nov. 11, 2019

(65) Prior Publication Data

US 2021/0139673 A1     May 13, 2021

(51) Int. Cl.
| | |
|---|---|
| *C08K 5/3492* | (2006.01) |
| *C07F 9/6521* | (2006.01) |
| *C07D 251/22* | (2006.01) |
| *C07D 251/46* | (2006.01) |
| *C08K 5/5397* | (2006.01) |
| *C08G 64/30* | (2006.01) |
| *C08K 5/5373* | (2006.01) |
| *C08K 5/50* | (2006.01) |
| *C08G 59/22* | (2006.01) |
| *C08G 59/50* | (2006.01) |

(52) U.S. Cl.
CPC .......... *C08K 5/3492* (2013.01); *C07D 251/22* (2013.01); *C07D 251/46* (2013.01); *C07F 9/6521* (2013.01); *C08G 59/22* (2013.01); *C08G 59/5086* (2013.01); *C08G 64/30* (2013.01); *C08K 5/50* (2013.01); *C08K 5/5373* (2013.01); *C08K 5/5397* (2013.01)

(58) Field of Classification Search
CPC .... C07D 251/22; C07D 251/46; C08G 64/30; C08G 59/22; C08G 59/5086; C08K 5/3492; C08K 5/5397; C08K 5/5375; C08K 5/50
See application file for complete search history.

(56) References Cited

U.S. PATENT DOCUMENTS

| | | | | |
|---|---|---|---|---|
| 3,900,443 A | * | 8/1975 | Luethi .................. | C08K 5/5373 524/100 |
| 5,350,848 A | * | 9/1994 | Cipolli ................ | C07F 9/65583 544/195 |

* cited by examiner

*Primary Examiner* — Patrick D Niland
(74) *Attorney, Agent, or Firm* — Dennis P. Clarke

(57) ABSTRACT

Trisubstituted triazines having the formula:

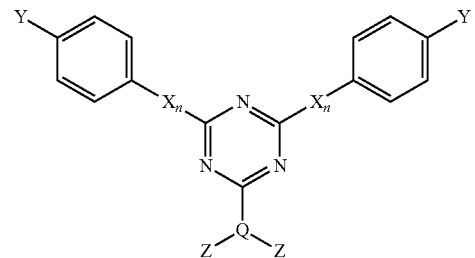

wherein:
X is O and n is 0 or 1,
Y is OH, $NH_2$ or $CH_2NH_2$,
Q is P, P=O, CH or N,
when Q is P, R is phenyl,
when Q is P=O, Z is R or OR, and R is alkyl or phenyl,
when Q is CH, Z is $PO(R)_2$ or $PO(OR)_2$,
when Q is N, Z is R, and
their uses as epoxy and cyclic carbonate polymer curing agents.

30 Claims, 6 Drawing Sheets

TRIAZINE COMPOUNDS, COMPOSITIONS, AND METHODS

BACKGROUND OF THE INVENTION

The invention relates to novel trisubstituted triazines, and their uses as epoxy and cyclic carbonate curing agents.

BRIEF SUMMARY OF THE INVENTION

An embodiment of the invention relates to compounds having the formula:

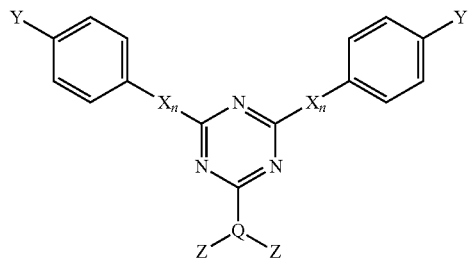

wherein:

X is O and n is 0 or 1,
Y is OH, $NH_2$ or $CH_2NH_2$,
Q is P, P=O, CH or N,
when Q is P, R is phenyl,
when Q is P=O, Z is R or OR, and R is alky or phenyl,
when Q is CH, Z is $PO(R)_2$ or $PO(OR)_2$, and
when Q is N, Z is R.

An additional embodiment of the invention is directed to methods for curing epoxy and/or cyclic carbonates employing the above compounds as curing agents.

Still further embodiments of the invention relate to

1] compositions for curing epoxy and/or cyclic carbonates comprising the above compounds and compatible carriers therefor,
2] compositions comprising epoxy and/or cyclic carbonates and flame-retardant, curing amounts of the above compounds, and
3] articles of manufacture comprising packaging material containing the above composition, wherein the packaging material contains instructions for the use thereof.

DETAILED DESCRIPTION OF THE INVENTION

The present invention is predicated on the unexpected discovery that certain novel tri-substituted triazines function as curing agents for epoxy and/or cyclic carbonates while also providing significant flame-retardant properties thereto.

Exemplary compounds of the invention described by the above generic formula include, but are not limited to:

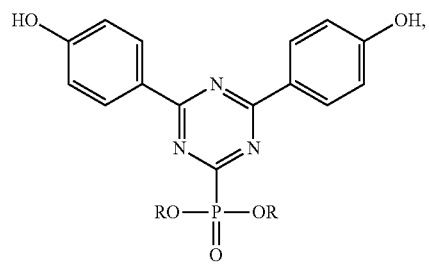

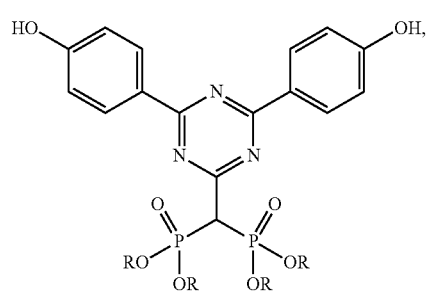

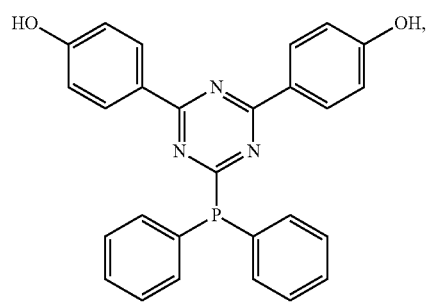

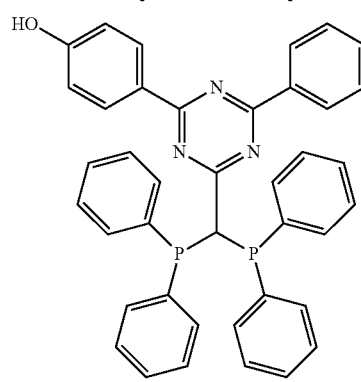

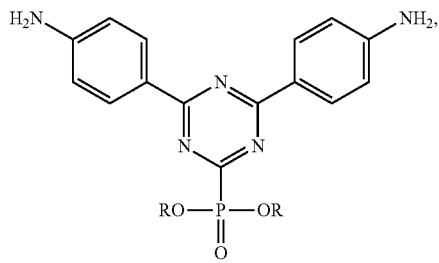

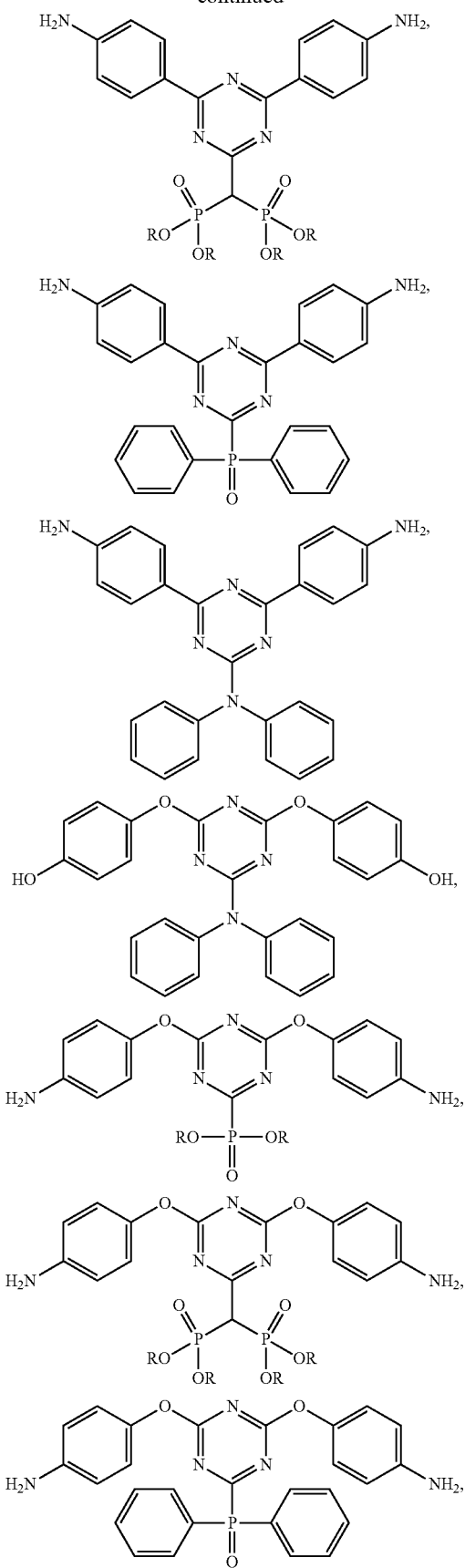
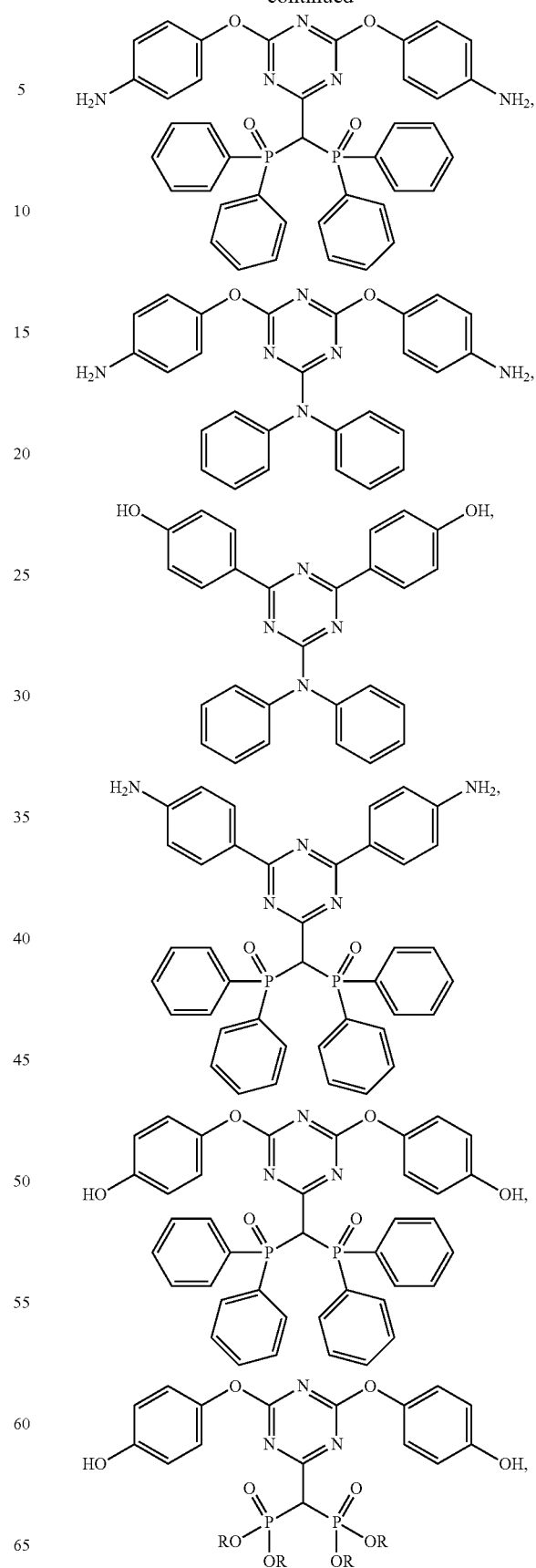

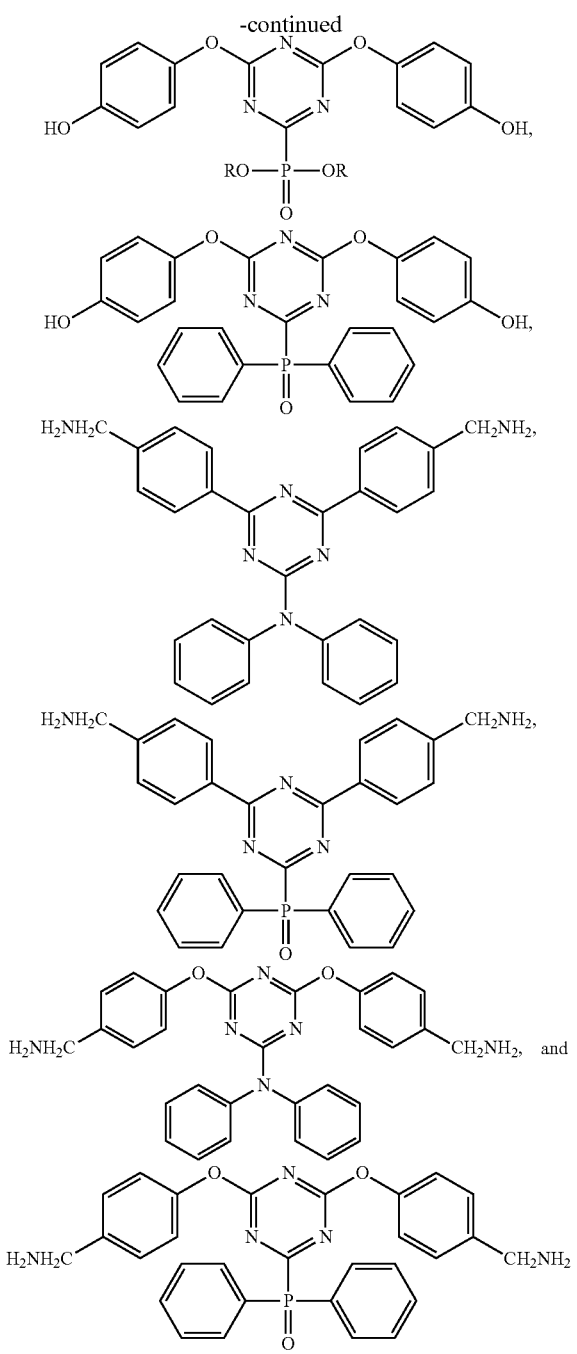

Figure 1:
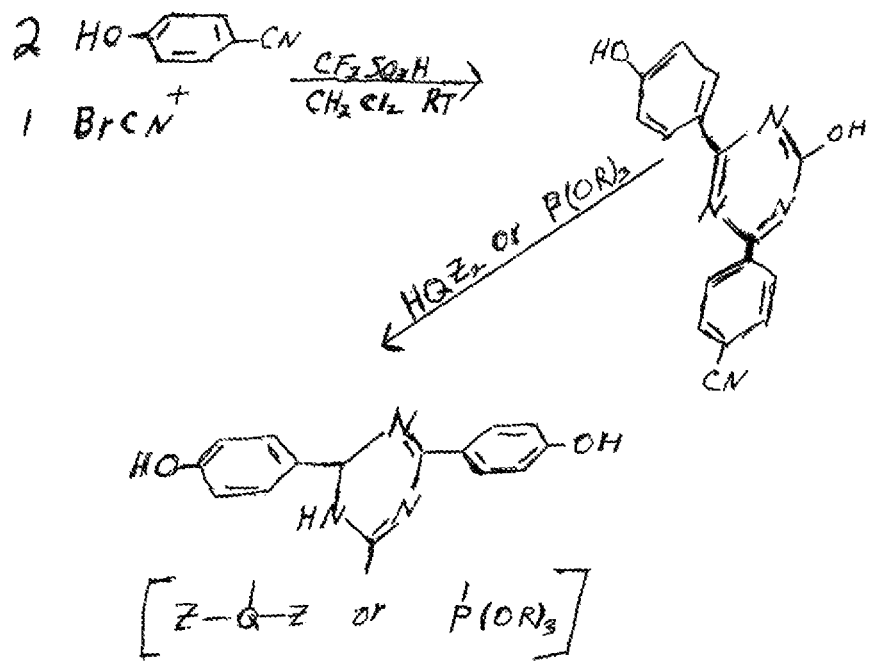
FIGS. 1-6 depict exemplary reaction schemes for the preparation of the compounds of the invention.
Figure 2:
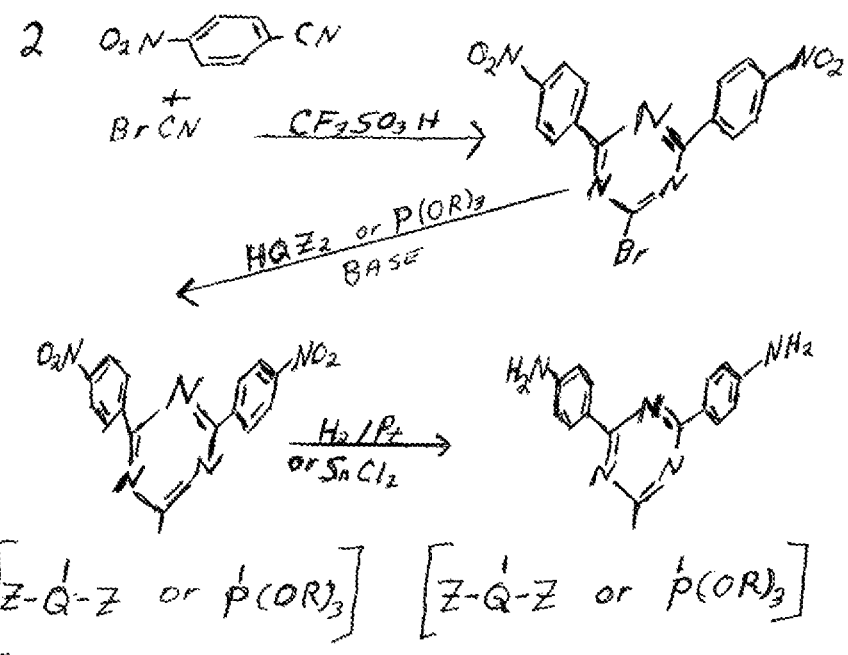

The compounds of the invention may be synthesized according to the reaction schemes set forth in FIGS. 1-6. Referring to FIGS. 1 and 2, the reaction of 1 and 2 in trifluoromethanesulfonic acid may be carried out as described in Halder et al; Angewandte Chemie—International Edition: vol. 55: nb. 27: (2016); pp. 7806-7810; Angew. Chem.; vol. 128: nb. 27; (2016); pp. 7937-7941. Alternatively, the reaction of 1 and 2 may be effected according to the procedure set forth in Forsberg et al; Journal of Heterocyclic Chemistry: vol. 25; (1988) pp. 767-770 or as described in Juarez et al; Tetrahedron Letters; vol. 46; nb. 51; (2005): pp, 8861-8864.

Figure 3:
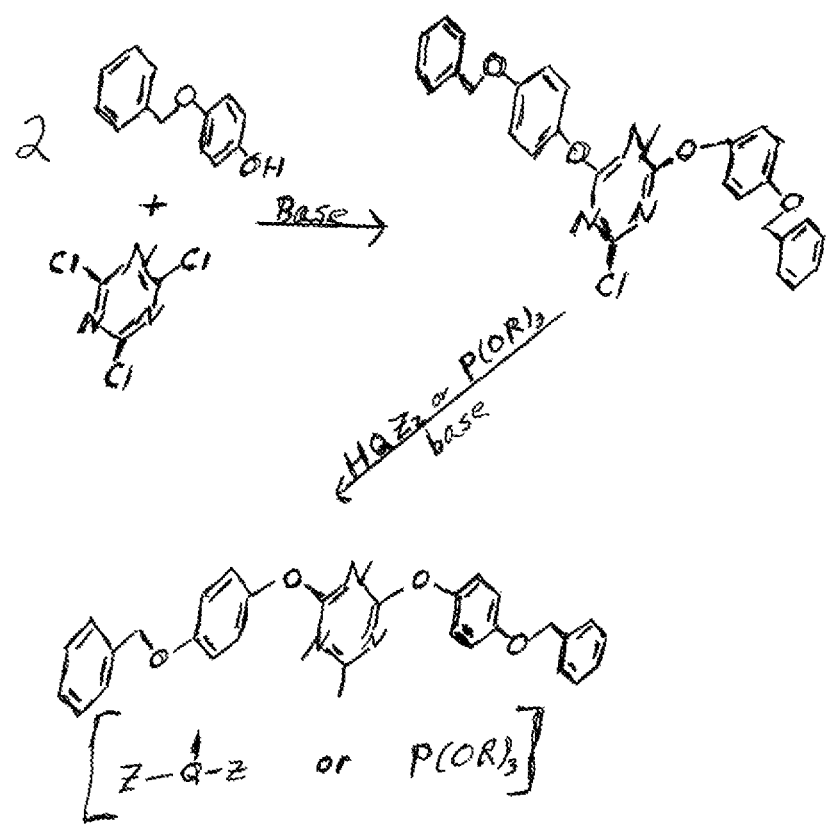
Figure 4:
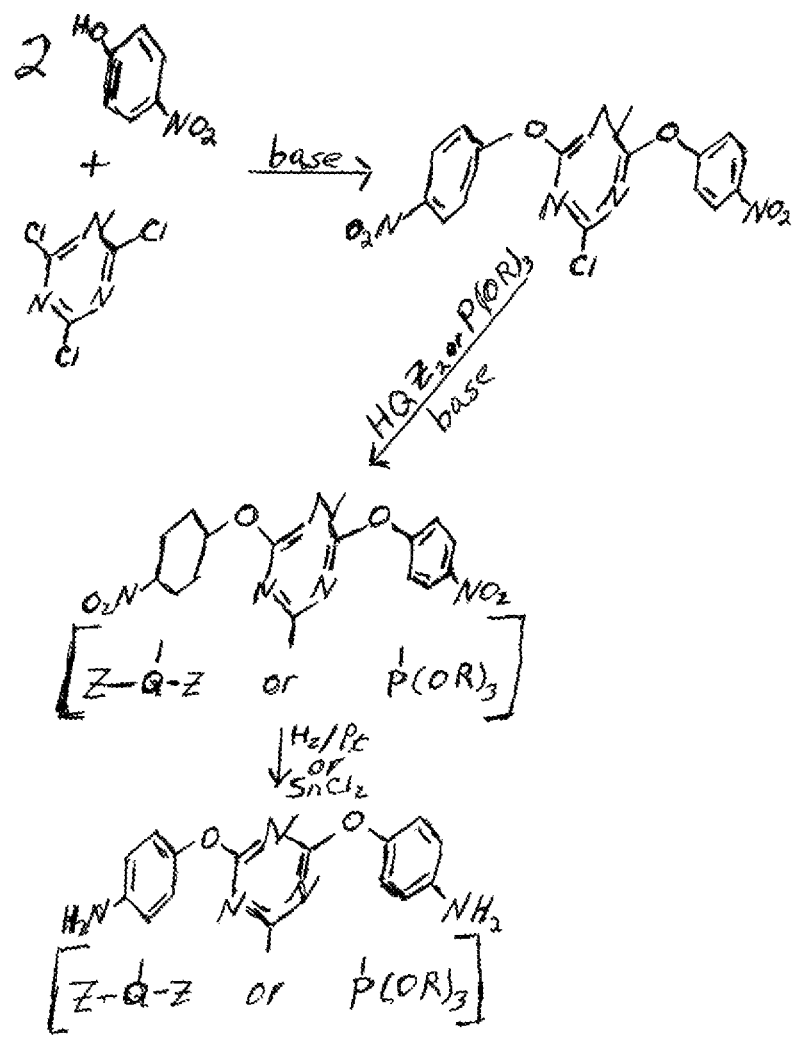
Figure 5:
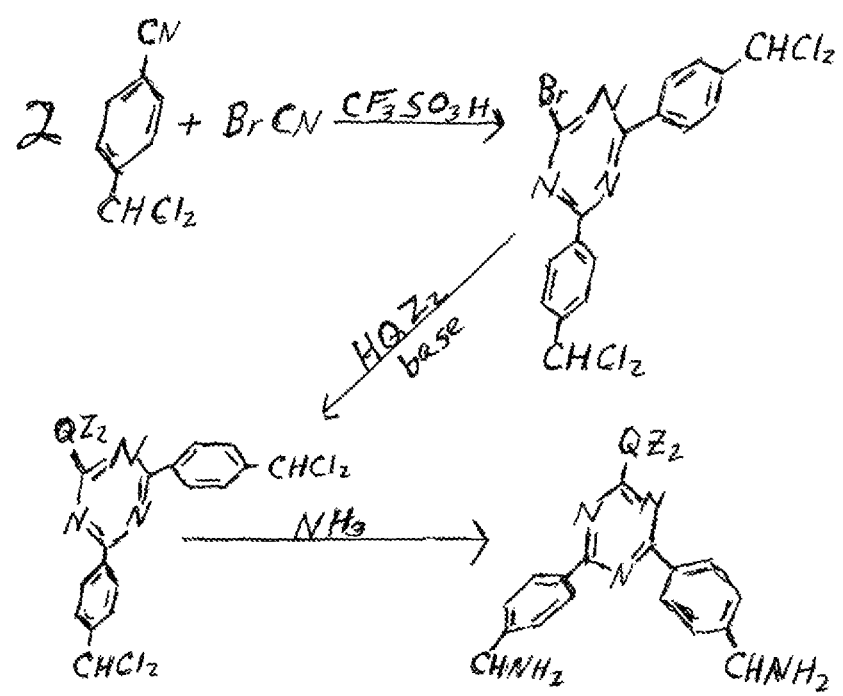
Figure 6:
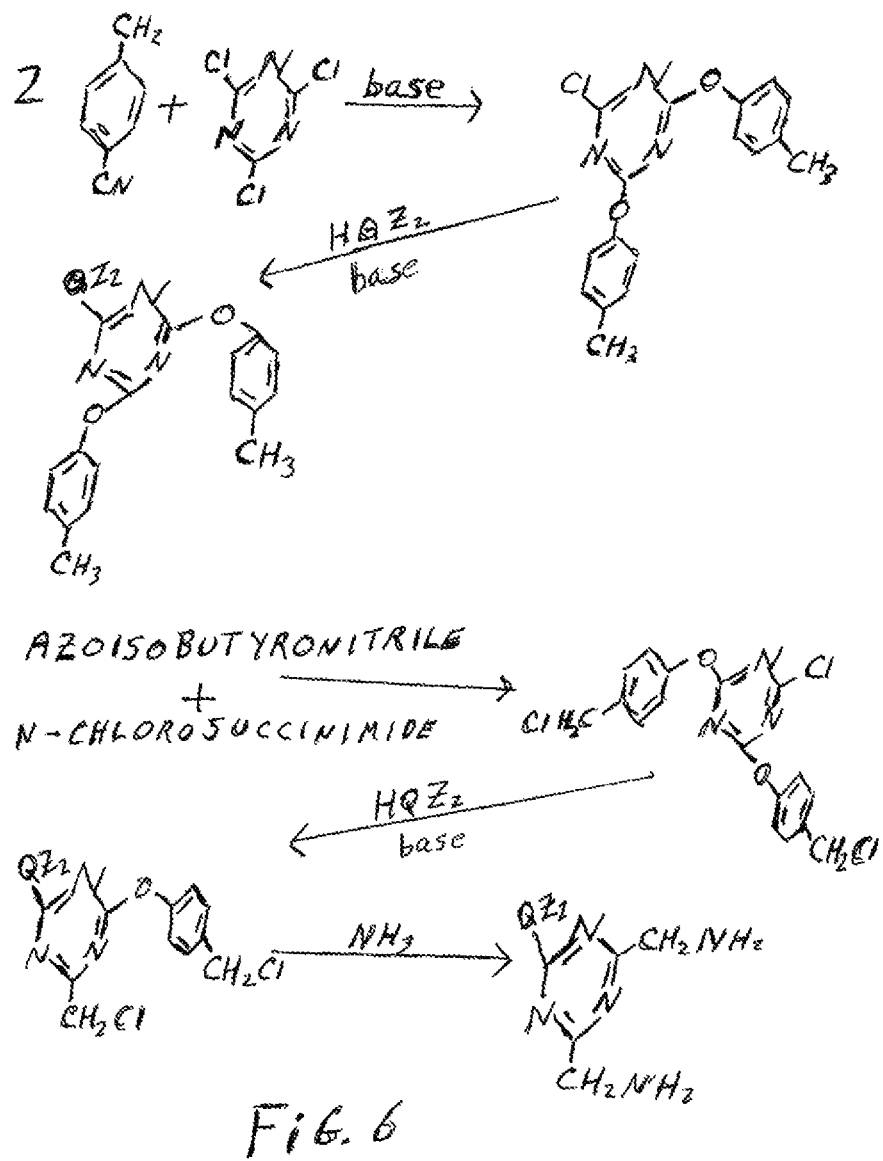

Referring to FIGS. 3 and 4, the first step of the synthesis may be conducted as set forth in Menicagli, et al; Synthetic Communications; vol. 24; nb. 15: (1994); pp 2153-2158.

Alternatively, the tri-substituted triazines of the invention may also be prepared as described in Samanta, Jayanta; Natarajan. Ramalingam; Organic Letters; vol. 18: nb. 14; (2016): p. 3394-3397; Kotha, Sambasivarao: Kashinath, Dhurke; Kumar, Sandeep: Tetrahedron Letters; vol. 49; nb. 37; (2008): p. 5419; Kotha, Sambasivarao; Kashinath, Dhurke; Lopus, Manu; Panda, Dulal; Indian Journal of Chemistry—Section B—Organic and Medicinal Chemistry; vol. 48: nb. 12; (2009): p. 1766-1770; Zhang, Rui-Feng; Hu, Wen-Jing; Liu, Yahu A.; Zhao, Xiao-Li; Li, Jiu-Sheng; Jiang, Biao; Wen, Ke: Journal of Organic Chemistry vol. 81; nb. 13; (2016); p. 5649-5654; Patent; Chinese Academy Of Sciences Shanghai Advanced Institute; Wen Ke: Wu Xinlang; Hu Wenjing; Zhang Ruifeng; Hu Weibo; Yang Yafen; Peng Lanzhen; Wang Guo: (24 pag.); CN108239099; (2018); (A) Chinese; Dash, Barada Prasanna; Satapathy, Rashmirekha; Maguire, John A.; Hosmane, Narayan S.; Organometallics; vol. 29; nb. 21; (2010): p. 5230-5235: Patent; JSR CORPORATION: NOSAKA, Naoya; WAKAMATSU, Gouji; ABE, Tsubasa; MATSUMURA, Yuushi: MIYAKE, Masayuki; TAKIMOTO, Yoshio; (21 pag.); US2019/94695: (2019); (A1) English; Maragani, Ramesh; Thomas, Michael B.; Misra, Rajneesh; D'Souza, Francis, Journal of Physical Chemistry A: vol. 122; nb. 21: (2018); p. 4829-4837; Zhou, Junfeng, Wang, Jiajia, Jin, Kaikai; Sun, Jing; Fang, Qiang; Polymer; vol. 102: (2016); p. 301-307; or Jena, Bibhuti Bhusan; Satish, Lakkoji; Mahanta, Chandra Sekhara: Swain, Biswa Ranjan; Sahoo, Harekrush-na; Dash, Barada P.; Satapathy, Rashmirekha: Inorganica Chimica Acta; (2019); p. 62-58.

Although tri-substituted triazines have previously been employed as curing agents (hardeners) for epoxies, the compounds of the present invention also provide significant and unexpected flame retardant properties to the resulting cured products.

"Epoxies" include, but is not limited to, monomers, oligomers, resins, or polymers with two or more epoxy groups per molecule, with no particular restrictions on the molecular weight or molecular structure, and examples include bisphenol-type epoxy resins such as bisphenol A-type epoxy resins, bisphenol F-type epoxy resins and teramethylbisphenol F-type epoxy resins, biphenyl-type epoxy resins such as biphenyl-type epoxy resins and tetramethylbiphenyl-type epoxy resins, crystalline epoxy resins such as stilbene-type epoxy resins and hydroquinone-type epoxy resins; novolac-type epoxy resins such as cresol-novolac-type epoxy resins, phenol-novolac-type epoxy resins and naphthol-novolac-type epoxy resins; phenolaralkyl-type epoxy resins such as phenylene backbone-containing phenolaralkyl-type epoxy resins, biphenylene backbone-containing phenolaralkyl-type epoxy resins, phenylene backbone-containing naphtholaralkyl-type epoxy resins and alkoxynaphthalene backbone-containing phenolaralkyl epoxy resins, trifunctional epoxy resins such as triphenol-methane-type epoxy resins and alkyl-modified triphenol-methane-type epoxy resins; modified phenol-type epoxy resins such as dicyclopentadiene-modified phenol-type epoxy resins and terpene-modified phenol-type epoxy resins; heterocyclic ring-containing epoxy resins such as triazine nucleus-containing epoxy resins; and phosphorus atom-containing epoxy resins, and any one or a combination of two or more thereof.

"Cyclic carbonates" or "cyclocarbonates" include, but are not limited to, those disclosed in U.S. Pat. Nos. 10,000,461; 9,667,313; 9,556,304; 8,153,042; 6,339,129; and 5,640,606, and any one or a combination of two or more thereof.

The amount of curing agent required will depend upon the epoxy or cyclocarbonate employed, but is generally in the range of from about 0.1 to about 10 parts by mass, preferably from about 0.1 to about 5 parts by mass based on 100 parts by mass of epoxy or cyclocarbonate.

The compounds of the invention may be added directly with the epoxy or cyclocarbonate W be cured, or they may be first be admixed with a suitable compatible carrier or solvent, such as, for example, those employed with conventional curing agents therefore.

Epoxies and cyclocarbonates may be cured, employing the curing agents of the invention, according to methods well known in the art, such as, for example, the methods disclosed in U.S. Pat. Nos. 6,809,161 and 6,541,119.

It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

We claim:

1. A compound having the formula:

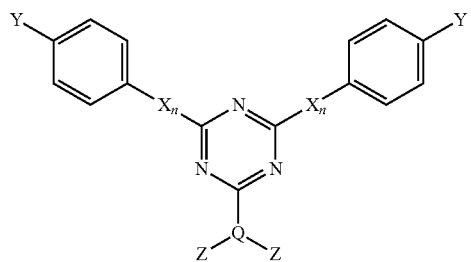

wherein:
X is O and n is 0 or 1,
Y is OH, $NH_2$ or $CH_2NH_2$,
Q is P, P=O, CH or N,
when Q is P, Z is phenyl,
when Q is P=O and n is 1, Z is R or OR, R is alkyl or phenyl, and Y is $NH_2$ or $CH_2NH_2$
when Q is P=O and n is 0, Z is R or OR, R is alkyl or phenyl, and Y is OH, NH2, or CH2NH2
when Q is CH, Z is $PO(R)_2$ or $PO(OR)_2$, R is alkyl or phenyl and
when Q is N, Z is phenyl.

2. A compound according to claim 1 having the formula:

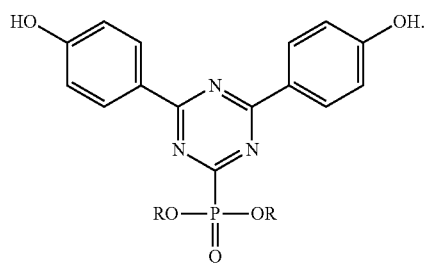

3. A compound according to claim 1 having the formula:

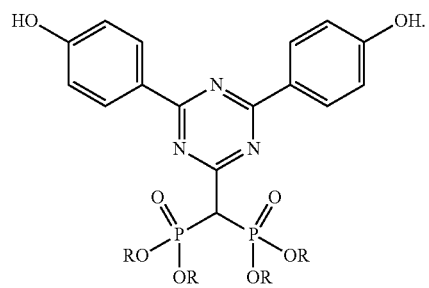

4. A compound according to claim 1 having the formula:

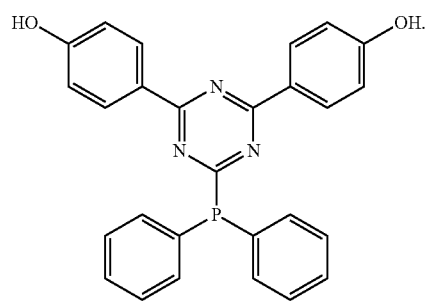 [SMILES: Oc1ccc(-c2nc(-c3ccc(O)cc3)nc(P(c3ccccc3)c3ccccc3)n2)cc1]

5. A compound according to claim 1 having the formula:

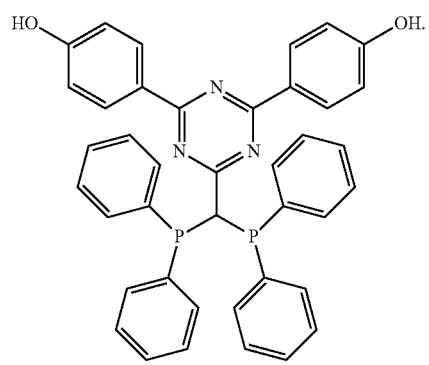 [SMILES: Oc1ccc(-c2nc(-c3ccc(O)cc3)nc(C(P(c3ccccc3)c3ccccc3)P(c3ccccc3)c3ccccc3)n2)cc1]

6. A compound according to claim 1 having the formula:

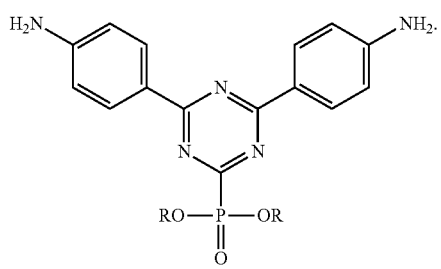

7. A compound according to claim 1 having the formula:

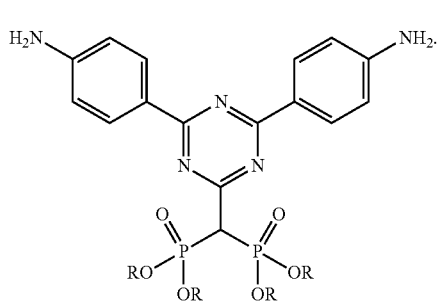

8. A compound according to claim 1 having the formula:

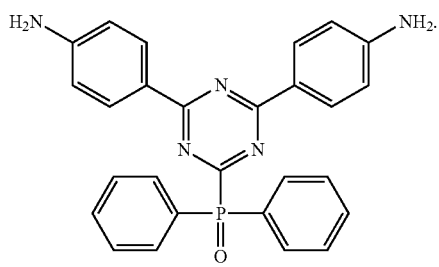 [SMILES: Nc1ccc(-c2nc(-c3ccc(N)cc3)nc(P(=O)(c3ccccc3)c3ccccc3)n2)cc1]

9. A compound according to claim 1 having the formula:

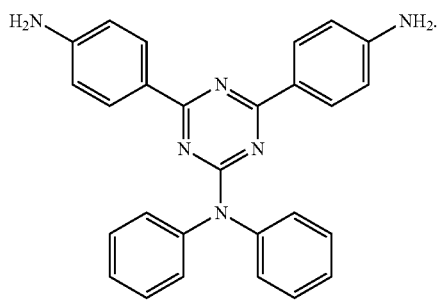 [SMILES: Nc1ccc(-c2nc(-c3ccc(N)cc3)nc(N(c3ccccc3)c3ccccc3)n2)cc1]

10. A compound according to claim 1 having the formula:

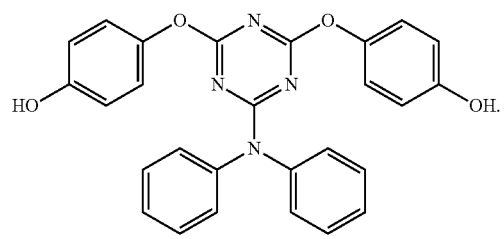 [SMILES: Oc1ccc(Oc2nc(Oc3ccc(O)cc3)nc(N(c3ccccc3)c3ccccc3)n2)cc1]

11. A compound according to claim 1 having the formula:

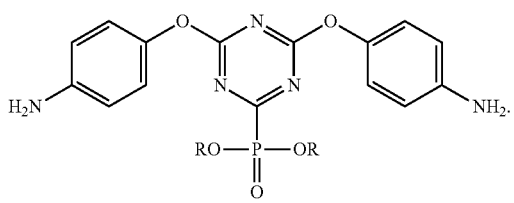

12. A compound according to claim 1 having the formula:

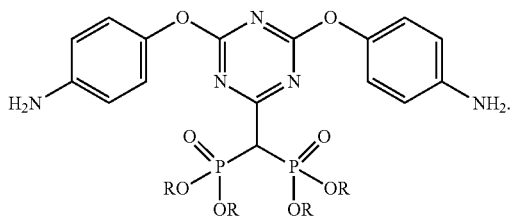

13. A compound according to claim 1 having the formula:

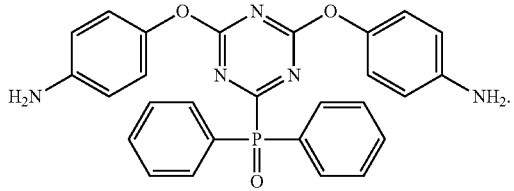 [SMILES: Nc1ccc(Oc2nc(Oc3ccc(N)cc3)nc(P(=O)(c3ccccc3)c3ccccc3)n2)cc1]

14. A compound according to claim 1 having the formula:

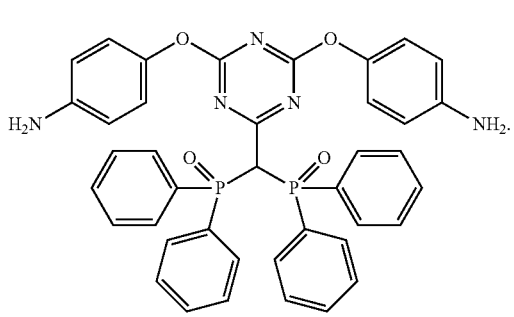 [SMILES: Nc1ccc(Oc2nc(Oc3ccc(N)cc3)nc(C(P(=O)(c3ccccc3)c3ccccc3)P(=O)(c3ccccc3)c3ccccc3)n2)cc1]

15. A compound according to claim 1 having the formula:

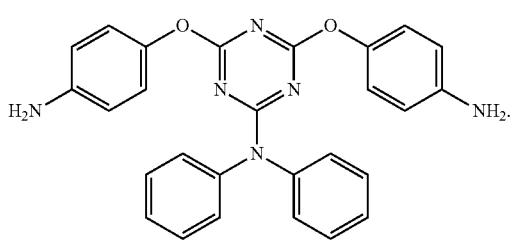 [SMILES: Nc1ccc(Oc2nc(Oc3ccc(N)cc3)nc(N(c3ccccc3)c3ccccc3)n2)cc1]

16. A compound according to claim 1 having the formula:

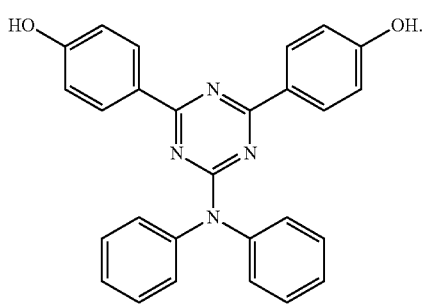

17. A compound according to claim 1 having the formula:

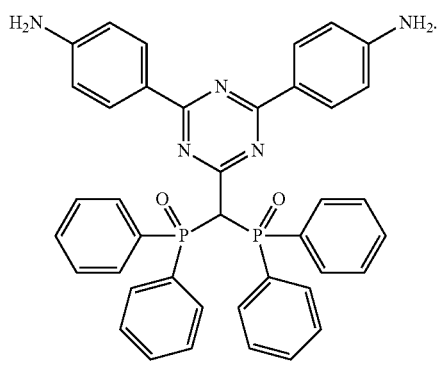 [SMILES: Nc1ccc(-c2nc(-c3ccc(N)cc3)nc(C(P(=O)(c3ccccc3)c3ccccc3)P(=O)(c3ccccc3)c3ccccc3)n2)cc1]

18. A compound according to claim 1 having the formula:

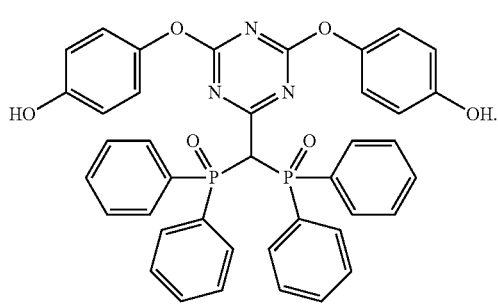 [SMILES: O=P(c1ccccc1)(c1ccccc1)C(c1nc(Oc2ccc(O)cc2)nc(Oc2ccc(O)cc2)n1)P(=O)(c1ccccc1)c1ccccc1]

19. A compound according to claim 1 having the formula:

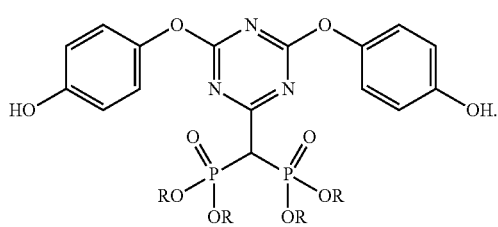

20. A compound according to claim 19 having the formula:

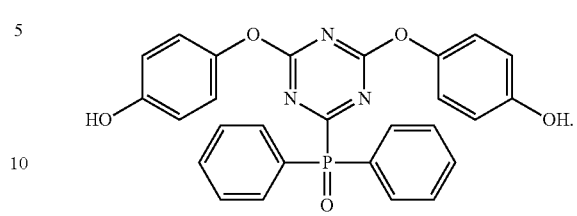

21. A compound according to claim 19 having the formula:

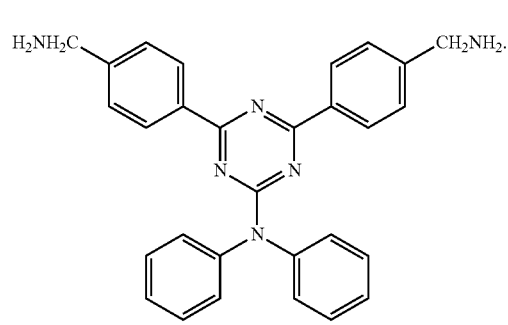

22. A compound according to claim 19 having the formula:

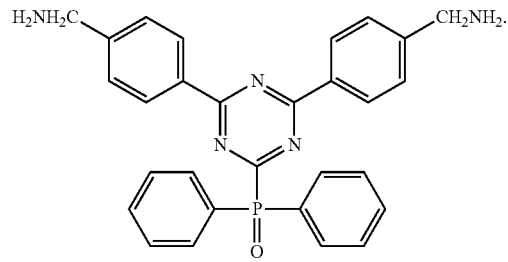

23. A compound according to claim 19 having the formula:

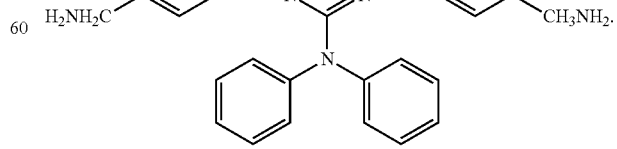

24. A compound according to claim 19 having the formula:

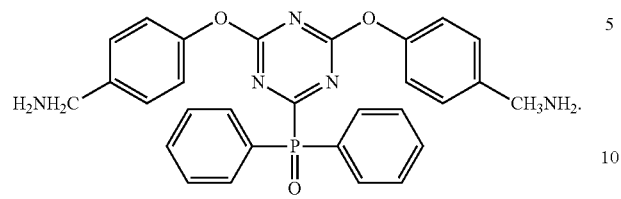

25. A flame retardant, epoxy and/or cyclic carbonate curing composition of matter comprising a compound of claim 19 and a carrier or solvent therefor.

26. A composition of matter comprising a curable epoxy and a flame retardant, epoxy curing amount of a composition of claim 25.

27. A composition of matter comprising a curable cyclic carbonate and a flame retardant, cyclic carbonate curing amount of a composition of claim 25, wherein Y is $CH_2-NH_2$.

28. A method of curing an epoxy comprising admixing therewith a flame retardant, epoxy curing amount of a composition of claim 26.

29. A method of curing a cyclic carbonate comprising admixing therewith a flame retardant, cyclic carbonate curing amount of a composition of claim 27.

30. An article of manufacture comprising packaging material containing the composition of claim 25, said packaging material containing instructions for the use thereof.

* * * * *